United States Patent
Peyman

(10) Patent No.: US 7,147,636 B1
(45) Date of Patent: Dec. 12, 2006

(54) METHOD AND APPARATUS FOR CORNEAL SHRINKAGE USING A PLURALITY OF ELECTRODES

(75) Inventor: Gholam A. Peyman, New Orleans, LA (US)

(73) Assignee: Minu, LLC, Pittsboro, NC (US)

(*) Notice: Subject to any disclaimer, the term of this patent is extended or adjusted under 35 U.S.C. 154(b) by 100 days.

(21) Appl. No.: 10/246,672

(22) Filed: Sep. 19, 2002

(51) Int. Cl.
*A61B 18/18* (2006.01)

(52) U.S. Cl. .................................. 606/50; 606/41
(58) Field of Classification Search .............. 606/4, 606/5, 32–34, 41, 42, 48–50
See application file for complete search history.

(56) References Cited

U.S. PATENT DOCUMENTS

| | | | | |
|---|---|---|---|---|
| 4,674,499 | A | * | 6/1987 | Pao .............................. 606/50 |
| 4,718,418 | A | | 1/1988 | L'Esperance |
| 4,840,175 | A | | 6/1989 | Peyman |
| 4,994,058 | A | | 2/1991 | Raven et al. |
| 5,336,261 | A | | 8/1994 | Barrett et al. |
| 5,413,574 | A | * | 5/1995 | Fugo ............................ 606/33 |
| 5,445,636 | A | * | 8/1995 | Bretton ........................ 606/41 |
| 5,533,999 | A | | 7/1996 | Hood et al. |
| 5,578,040 | A | * | 11/1996 | Smith .......................... 606/41 |
| 5,749,871 | A | | 5/1998 | Hood et al. |
| 6,142,996 | A | * | 11/2000 | Mirhashemi et al. ........ 606/41 |
| 6,213,997 | B1 | * | 4/2001 | Hood et al. .................... 606/5 |
| 6,280,470 | B1 | | 8/2001 | Peyman |
| 2002/0111608 | A1 | * | 8/2002 | Baerveldt et al. .............. 606/6 |
| 2002/0120260 | A1 | * | 8/2002 | Morris et al. .................. 606/41 |

OTHER PUBLICATIONS

Jose I. Barraquer, M.D., entitled "Keratomileusis and Keratophakia in the Surgical Correction of Aphakia", pp. 270-289.
Daniel S. Durrie, M.D., entitled "CK-Beyond Hyperopia", supplemental to Cataract & Refractive Surgery Today, Apr. 2002, pp. 27-28.
Marquerite B. McDonald, M.D. et al., "Conductive Keratoplasty for the Correction of Low to Moderate Hyperopia", Ophthalmology vol. 109, No. 4, Apr. 2002, pp. 637-650.
Ed Edelson, "Lasik surgeon continually fine-tunes his technique", Jun. 15, 2000/Opthalmology Times, p. 24.
Cheryl Guttman, "Conductive keratoplasty used to correct hyperopia", Jun. 15, 2000/Ophthalmolgy Times, pp. 22-23.
Ishizaki et al., *Expression of Collagen I, Smooth Muscle α-Actin, and Vimentin During the Healing of Alkali-Burned and Lacerated Corneas*, Investigative Ophthalmology & Visual Science, Nov. 1993, vol. 34, No. 12, pp. 3320-3328.

* cited by examiner

*Primary Examiner*—Michael Peffley
(74) *Attorney, Agent, or Firm*—Bell, Boyd & Lloyd, LLC; Jeffrey J. Howell

(57) ABSTRACT

A device for reshaping the cornea to correct the refractive error thereof. A first electrode is adapted to be heated and inserted into the corneal stroma of the eye, thereby reshaping a portion of the cornea. A second electrode is adapted to be heated and inserted into the corneal stroma of the eye, thereby reshaping a portion of the cornea. A member couples the first and the second electrodes together, allowing for change of the refractive power of the cornea, while avoiding irregular shrinkage of the corneal tissue.

15 Claims, 2 Drawing Sheets

METHOD AND APPARATUS FOR CORNEAL SHRINKAGE USING A PLURALITY OF ELECTRODES

FIELD OF THE INVENTION

The present invention relates to a method and apparatus for correcting the refractive error in the eye using a plurality of electrodes. More particularly, the present invention relates to a method and apparatus for correcting refractive error in the cornea of an eye using a plurality of electrodes that are coupled together and simultaneously inserted into the eye. The electrodes, when heated, cause the tissue in the cornea to shrink, and therefore change the refractive power of the cornea.

BACKGROUND OF THE INVENTION

A normal emetropic eye includes a cornea, a lens and a retina. The cornea and lens of a normal eye cooperatively focus light entering the eye from a far point, i.e., infinity, onto the retina. However, an eye can have a disorder known as ametropia, which is the inability of the lens and cornea to focus the far point correctly on the retina. Typical types of ametropia are myopia, hypermetropia or hyperopia, and astigmatism.

A myopic eye has either an axial length that is longer than that of a normal emetropic eye, or a cornea or lens having a refractive power stronger than that of the cornea and lens of an emetropic eye. This stronger refractive power causes the far point to be projected in front of the retina.

Conversely, a hypermetropic or hyperopic eye has an axial length shorter than that of a normal emetropic eye, or a lens or cornea having a refractive power less than that of a lens and cornea of an emetropic eye. This lesser refractive power causes the far point to be focused behind the retina.

An eye suffering from astigmatism has a defect in the lens or shape of the cornea. Therefore, an astigmatic eye is incapable of sharply focusing images on the retina.

Optical methods are known which involve the placement of lenses in front of the eye, for example, in the form of eyeglasses or contact lenses, to correct vision disorders. A common method of correcting myopia is to place a "minus" or concave lens in front of the eye to decrease the refractive power of the cornea and lens. In a similar manner, hypermetropic or hyperopic conditions can be corrected to a certain degree by placing a "plus" or convex lens in front of the eye to increase the refractive power of the cornea and lens. Lenses having other shapes can be used to correct astigmatism. The concave, convex or other shaped lenses are typically configured in the form of glasses or contact lenses.

Although these optical methods can be used to correct vision in eyes suffering from low myopia, or in eyes suffering from hypermetropic, hyperopic or astigmatic conditions which are not very severe, these methods are ineffective in correcting vision in eyes suffering from severe forms of ametropia.

However, surgical techniques exist for correcting these more severe forms of ametropia to a certain degree. For example, in a technique known as myopic keratomileusis, a microkeratome is used to cut away a portion of the front of the live cornea from the main section of the live cornea. The cut portion of the cornea is frozen and placed in a cryolathe where it is cut and reshaped. Altering the shape of the cut portion of the cornea changes the refractive power of this cut portion, which thus affects the location at which light entering the cut portion of the cornea is focused. The reshaped cut portion of the cornea is then thawed and reattached to the main portion of the live cornea. Hence, it is intended that the reshaped cornea will change the position at which the light entering the eye through the cut portion is focused, so that hopefully the light is focused directly on the retina, thus remedying the ametropic condition.

The myopic keratomileusis technique is known to be effective in curing myopic conditions within a high range. However, the technique is impractical because it employs very complicated and time consuming freezing, cutting and thawing processes.

Keratophakia is another known surgical technique for correcting severe ametropic conditions of the eye by altering the shape of the eye's cornea. In this technique an artificial, organic or synthetic lens is implanted inside the cornea to thereby alter the shape of the cornea and thus change its refractive power. Accordingly, as with the myopic keratomileusis technique, it is desirable that the shape of the cornea be altered to a degree that allows light entering the eye to be focused correctly on the retina.

However, the keratophakia technique is relatively impractical, complicated, and expensive because it requires manufacturing or cutting a special lens prior to its insertion into the cornea. Hence, a surgeon is required to either maintain an assortment of many differently shaped lenses, or alternatively, must have access to expensive equipment, such as a cyrolathe, which can be used to cut the lens prior to insertion into the cornea.

Examples of known techniques for modifying corneal curvature, such as those discussed above, are described in U.S. Pat. No. 4,994,058 to Raven et al., U.S. Pat. No. 4,718,418 to L'Esperance, U.S. Pat. No. 5,336,261 to Barrett et al., and a publication by Jose I. Barraquer, M.D. entitled "Keratomileusis and Keratophakia in the Surgical Correction of Aphakia". The entire contents of each of these patents are incorporated herein by reference.

Surgical techniques involving the use of ultraviolet and shorter wavelength lasers to modify the shape of the cornea also are known. For example, excimer lasers, such as those described in U.S. Pat. No. 4,840,175 to Peyman, which emit pulsed ultraviolet radiation, can be used to decompose or photoablate tissue in the live cornea so as to reshape the cornea.

Specifically, a laser surgical technique known as laser in situ keratomileusis (LASIK) has been previously developed by the present inventor. In this technique, a portion of the front of a live cornea can be cut away in the form of a flap having a thickness of about 160 microns. This cut portion is removed from the live cornea to expose an inner surface of the cornea. A laser beam is then directed onto the exposed inner surface to ablate a desired amount of the inner surface up to 150–180 microns deep. The cut portion is then reattached over the ablated portion of the cornea and assumes a shape conforming to that of the ablated portion.

However, because only a certain amount of cornea can be ablated without the remaining cornea becoming unstable or experiencing outwardbulging (eklasia), this technique is not especially effective in correcting very high myopia. That is, a typical live cornea is on average about 500 microns thick. The laser ablation technique requires that at least about 200 microns of the corneal stroma remain after the ablation is completed so that instability and outwardbulging does not occur. Hence, this method typically cannot be effectively used to correct high myopia of greater than 15 diopters because, in order to reshape the cornea to the degree necessary to alter its refractive power to sufficiently correct the focusing of the eye, too much of the cornea would need to be ablated.

Additionally, the cornea can be modified using thermal coagulation. In thermal coagulation, electrodes of varying shapes (generally about 450 microns long and 50 microns in diameter) are inserted through the exterior surface of the cornea in a predetermined pattern. The electrodes emit a radio frequency wave or laser light, thereby heating the surface of the cornea. Once the surface of the cornea is heated it tends to coagulate around the electrode and shrink, the shrinking of the cornea changes the refractive properties of the eye. In the conventional form of these methods, each application of the electrodes requires removal of the electrode and its insertion into a new location in the cornea. This sequential insertion into multiple locations is very imprecise and the entire time period for inserting the electrode into the cornea is relatively long, resulting in irregular shrinkage of the cornea. Furthermore, by inserting the electrodes through the exterior surface of the cornea, the electrodes will shrink both the epithelial layer and the Bowman's layer in the eye. This can result in irregular shrinkage of the cornea, leading to astigmatic problems and possibly cloudiness formed during the healing process.

For examples of known techniques for modifying visual activity by thermal means, see U.S. Pat. Nos. 5,533,989 and 5,749,871, both to Hood et al.

Therefore, it is apparent that a need therefore exists for improved methods for further modifying the cornea to better correct the refractive error therein.

SUMMARY OF THE INVENTION

Accordingly, it is an object of the present invention to provide a method and apparatus for adjusting the shape of a live cornea to correct the refractive error in the cornea.

Another object of the invention is to provide a method and apparatus for modifying the shape of a live cornea to correct refractive error in the cornea without laser ablation.

Another object of the present invention is to provide a method and apparatus for adjusting the shape of a live cornea by heating the cornea so that it shrinks and reforms, thereby changing the refractive power of the cornea.

A further object of the present invention is to provide a method and apparatus for modifying the cornea of an eye that allows for corrective measures that avoid or eliminate outwardbulging or instability in the cornea.

Still another object of the present invention is to provide a method and apparatus for changing the refractive power of the cornea that avoids irregular shrinkage of the corneal tissue.

Yet another object of the present invention is to provide a method and apparatus for modifying the cornea of an eye that can be used for at least hyperopic and astigmatic correction of refractive errors.

Still yet another object of the present invention is to provide a method and apparatus for modifying the cornea of the eye that coagulates the cornea under a flap directly in the stromal layer of the eye.

The foregoing objects are basically attained by a method of correcting refractive error in the cornea of an eye, comprising the steps of coupling a plurality of electrodes together and heating the plurality of electrodes to a predetermined temperature. The surface of the cornea is separated into first and second surfaces, and the plurality of electrodes are inserted into at least one of said first and second surfaces at generally the same time for a predetermined period of time. The electrodes are then removed, thereby reshaping the cornea to correct the refractive error in the eye.

The foregoing objects are further attained by a device for reshaping the cornea to correct the refractive error thereof, including first and second electrodes adapted to be heated and inserted into the corneal stroma of the eye, thereby reshaping a portion of the cornea. A member couples the first and the second electrodes together.

The foregoing objects are further attained by a first electrode having a first electrical pole adapted to be inserted into the cornea, and a second electrode having a second electrical pole, opposite said first electrical pole, and adapted to be inserted into the cornea. The second electrode is coupled to the first electrode, so that when a portion of the first electrode is inserted into the cornea, a portion of said second electrode is inserted into the cornea. A power source supplies electricity to the first and second electrodes, so that the electricity passes from said first electrical pole through said cornea and to said second electrical pole.

Other objects, advantages, and salient features of the present invention will become apparent to those skilled in the art from the following detailed description, which, taken in conjunction with the annexed drawings, discloses preferred embodiments of the invention.

BRIEF DESCRIPTION OF THE DRAWINGS

Referring to the drawings which form a part of this disclosure.

DETAILED DESCRIPTION OF THE INVENTION

Figure 1:
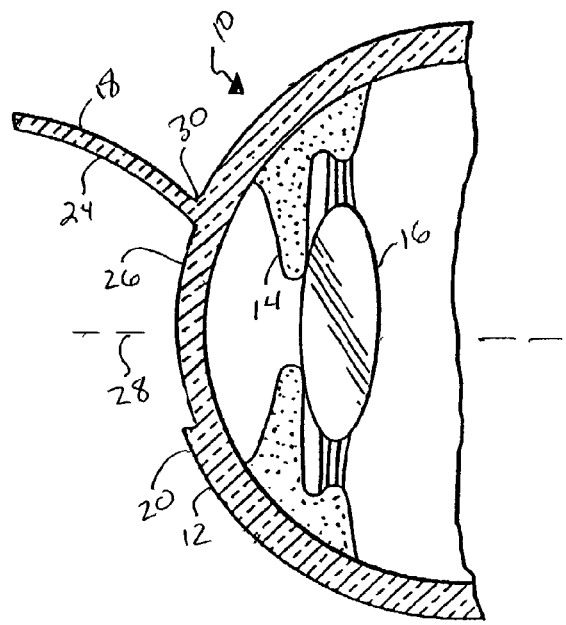
FIG. 1 is a side elevational view in cross section taken through the center of an eye showing the cornea, pupil and lens, with a flap formed in the surface of the cornea.

FIG. 1 is a side elevational view in cross section taken through the center of an eye 10, which includes a live cornea 12, a live pupil 14 and a live lens 16. If the cornea 12 and lens 16 do not cooperatively focus light correctly on the retina (not shown) of the eye to thus provide adequate vision, the curvature of the cornea can be modified to correct the refractive power of the cornea and thus correct the manner in which the light is focused with respect to the retina.

As seen in FIGS. 1–6, the refractive properties of the eye can be modified or altered by forming a flap 18 in the outer surface 20 of the cornea, and heating the cornea using a reshaping device 22. Since the cornea is reshaped via coagulation of the cornea, which causes shrinkage of the corneal tissue, this method is particularly effective for hyperopia and astigmatism.

To begin, the refractive error in the eye is measured using wavefront technology, as is known to one of ordinary skill in the art. The refractive error measurements are used to determine the appropriate shape of the cornea that would be best to correct the error in the patient's cornea.

Preferably the flap 18 is then formed in the stromal layer of the cornea, but does not necessarily need to be formed in the stromal layer and can be formed in any desired portion of the cornea. The flap may be formed be any means desired, such as with a knife, microkeratome, or with a laser. Preferably an internal area of the cornea is separated into first and second substantially circular shaped internal surfaces 24 and 26, respectively, to form the circular shaped corneal flap 18. First internal surface 24 faces in a posterior direction of cornea 12 and the second internal surface 26 faces in anterior direction of the cornea 12. The flap 18 preferably has a uniform thickness of about 10–250 microns, and more preferably about 80–100 microns, but can be any suitable thickness. A portion 30 of flap 18 preferably remains attached to the cornea by an area at the periphery of the flap. However, the flap can be any suitable configuration, such as a flap attached to the cornea at a location other than at the periphery or a flap that is not attached to the cornea at all. For example, the flap can be attached to the cornea at the center of the flap, i.e. at an area about the central optical axis 28 of the eye. For a more detailed description of this type of flap see U.S. Pat. No. 6,280,470 to Peyman, the entire contents of which are incorporated herein by reference. Additionally, the flap may be shaped or sized as desired and does not need to be circular.

The flap is moved or pivoted about portion 30 using any device known in the art, such as a spatula or microforceps or any other device, to expose the first and second corneal surfaces 24 and 26, respectively. The flap preferably exposes a portion of the corneal surface that intersects the main optical axis 28 and allows uninhibited access thereto.

The reshaping device 22 is then positioned adjacent one of the exposed surfaces 24 and/or 26. The reshaping device preferably has a plurality of heated electrodes, or heating elements, 32 that are inserted into the cornea, and thereby cause shrinkage of a portion of the cornea, altering the refractive properties thereof.

Figure 2:
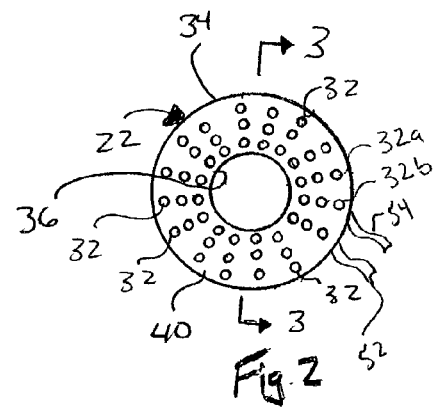
FIG. 2 is a bottom plan view of a cornea reshaping device according to an embodiment of the present invention.
Figure 3:
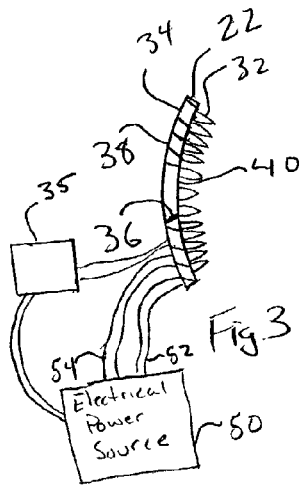
FIG. 3 is a side elevation view in cross section of the cornea reshaping device of FIG. 2, taken along lines 3—3.

As seen specifically in FIGS. 2 and 3, the reshaping device preferably has a substantially circular or substantially ring-shaped plate or member 34 with an aperture or opening 36 extending through the center, and a plurality of electrodes 22 extending from the plate. The plate can be formed of metal or plastic or any other rigid or semi-rigid suitable material and can be curved in the form of a portion of a hemisphere to fit the natural curvature of the cornea 12. It is noted that the plate 34 does not necessarily need to be curved to fit the natural curvature of the cornea and may be formed of a pliable material, so that it will conform to the curvature of the cornea once applied thereto. Furthermore, the plate can be any shape desired and does not need to be circular or ring-shaped. For example, the plate can be any polygon and does not need to have an opening therein.

Plate 34 has a first or top surface 38 and a second or bottom surface 40. Preferably, second surface 40 is adapted to be positioned adjacent the exposed surface of the cornea 32. However, if desired, the second surface can be placed adjacent the first surface 38. Furthermore, it is noted that although it is preferable to position the plate 34 on an exposed surface under flap 18, this is not necessary. For example, the plate can be positioned on the outer surface 20 of the cornea.

Preferably at least about 10 to about 12 electrodes 24 extend from the second surface 40 and are preferably each about 150 to about 450 microns in length and about 50 to 100 microns in width. Each electrode can preferably deliver a low energy, high frequency current directly to the cornea by means of a keratoplast tip, as is known in the art. Furthermore, each electrode preferably is substantially similar to each other electrode extending from the plate. However, the number of electrodes can be any number desired, as long as they number greater than one, and each electrode can be any shape and size desired to penetrate into the cornea.

The electrodes preferably form a substantially circular ring around the center or opening 36 of the plate 34 and are evenly spaced therearound. Furthermore, the electrodes preferably form one row, with each electrode being about the same distance from the center of the plate as each other electrode. However, it is noted that, as shown in FIG. 2, the electrodes can number greater than ten or twelve and be any plurality desired and can form two or three or more rows of electrodes evenly spaced about the plate with each electrode being about the same distance from the center of the plate as each other electrode in the same row. Furthermore, the electrodes can be placed in any position or pattern about the opening, if desired, or on any position on a plate with or without an opening. Any positioning of a plurality of electrodes on the plate will result in a predictable pattern of heating of the cornea and therefore a predictable result for the correction of the refractive error in the cornea.

The plate and/or electrodes are preferably coupled to an electrical power source 50 via wires 52 and 54. The power source is capable of heating the electrodes to a predetermined temperature for a predetermined amount of time. Furthermore, as shown in FIG. 3, a device or temperature control system 35 can monitor or measure the temperature of the probes 32, and shut off or regulate the electrical power to the probes to control the duration and the temperature of the heating the cornea.

Preferably first electrode 32a has a first electrical pole and a second electrode 32b has a second electrical pole, which is opposite the first electrical pole. When the electricity is supplied from the power source 50, it passes from the first electrical pole through the cornea and into the second electrical pole.

Furthermore, it is not necessary to use electrical current in the electrodes. For example, each electrode can be a probe that emits microwaves or radio waves at a predetermined frequency. By using one of these types of media, it is not necessary to ground the patient's body during the procedure.

As the plate 34 is being positioned adjacent the surface of the cornea, each electrode is inserted into the cornea, preferably into the stroma or the stromal layer. By inserting the electrodes directly into the stroma of the cornea, the electrodes do not enter or pass through the epithelial layer or the Bowman's layer in the cornea. By avoiding these two layers, the cornea is much less likely to become cloudy or have irregular shrinkage, which can result in astigmatic error. The stromal layer will heal in a much more predictable and reliable pattern, thus avoiding possible astigmatic problems. Additionally, the stromal layer will not become cloudy as readily as the epithelial layer or the Bowman's layer. Furthermore, inserting the electrodes in this manner allows the flap to smooth out any possible imperfections in the exposed surface of the cornea, and further assure that any astigmatic imperfections are eliminated or substantially eliminated.

Figure 4:
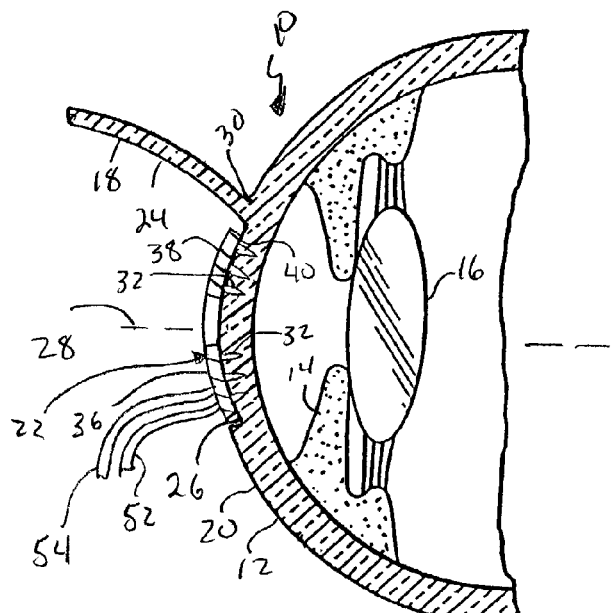
FIG. 4 is a side elevational view in cross section of the eye of FIG. 1 with the cornea reshaping device proximate to the exposed surface of the cornea.

As seen in FIG. 4, the plate is positioned so that the opening 36 is generally centered about the main optical axis 28, with the electrodes entering the cornea in a ring pattern centered around the main optical axis. This allows the cornea through which the main optical axis passes to remain unaffected, while still altering the refractive properties of the cornea.

Since each electrode is preferably substantially the same length as each other electrode coupled to the plate, the electrodes are simultaneously or substantially simultaneously inserted into the cornea. Furthermore, each electrode's position relative to each other electrode and relative to main optical axis of the cornea is known, and can therefore be precisely monitored.

Each electrode is then simultaneously or substantially simultaneously heated using any known or desired heating device. For example, the electrodes and/or plate can be electrically coupled to a heating source 50 via electrical wires 52 and 54 and a switch adapted to heat the electrodes at a predetermined temperature for a predetermined period of time. Preferably, the electrodes are heated to a temperature between about 55° C. and about 75° C. for a relatively short time (i.e., preferably 2–3 second or less, and more preferably less than 1 second). By inserting and heating the electrodes in this manner, the corneal tissue can be heated in a very regular and predictable time frame.

Figure 5:
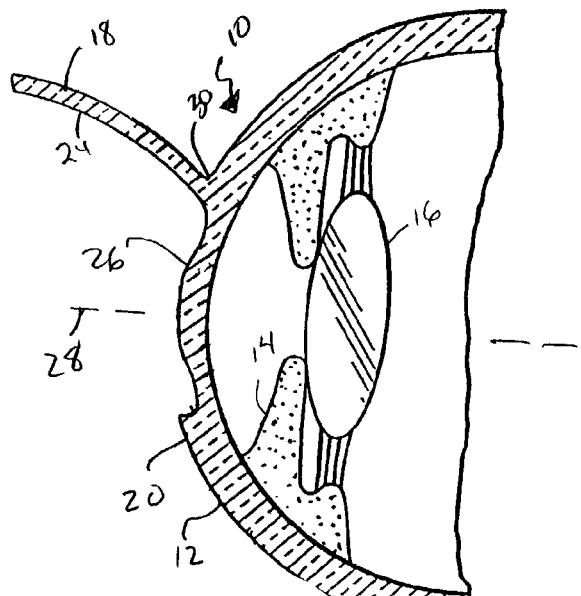
FIG. 5 is a side elevational view in cross section of the eye of FIG. 4 with the reshaping device removed and the cornea maintaining its reformed shape.

Once the electrodes heat the corneal tissue, the tissue coagulates around each electrode, causing precise tissue coagulation and shrinkage of the cornea and changing the refractive properties of the cornea in a predictable manner. Preferably, once the electrodes are removed, the cornea shrinks in a substantially ring-shaped pattern surrounding the main optical axis, therefore correcting hyperopia, as shown in FIG. 5.

It is noted that the electrodes do not necessarily need to be heated using electricity via wires and can be heated in any manner desired, such as using a laser or heated water, or any other method or device known to one skilled in the art. Furthermore, more than one of the above-described methods could be used simultaneously (i.e., electrical heating and laser heating, etc.).

Figure 6:
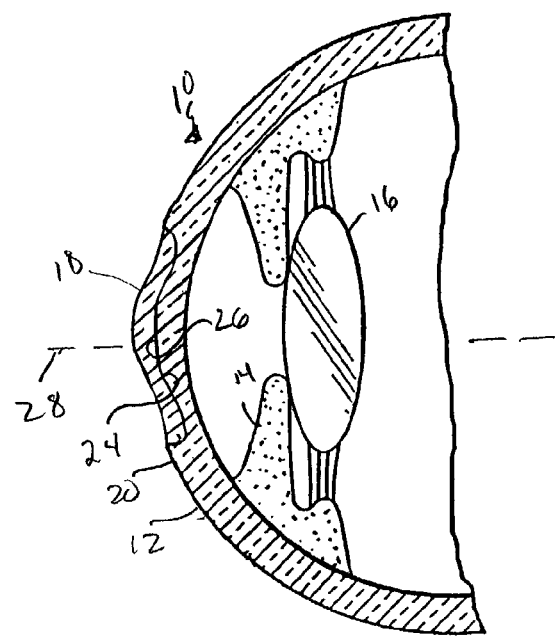
FIG. 6 is a side elevational view in cross section of the eye of FIG. 5 with the flap repositioned over the reformed exposed surface of the cornea.

The flap 18 is then replaced so that first surface 24 and second surface 26 are adjacent one another in a relaxed state, as seen in FIG. 6. This new permanent shape allows the cornea to properly focus light entering the eye on the retina. The refractive power of the eye is then measured to determine the extent of the correction. If necessary the method can be repeated.

By reforming the cornea into the desired shape in this manner, a highly effective method is provided that allows near perfect vision correction without the need to ablate any of the cornea.

Figure 8:
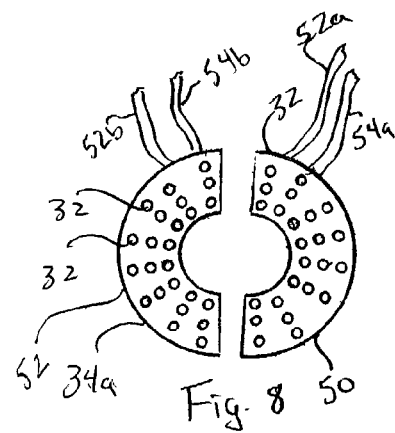
FIG. 8 is a bottom plan view of a cornea reshaping device according to a third embodiment of the present invention.
Figure 7:
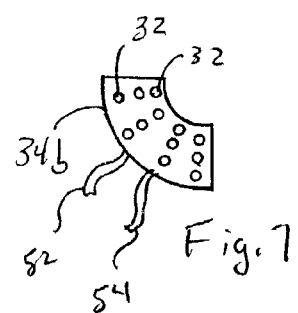
FIG. 7 is a bottom plan view of a cornea reshaping device according to a second embodiment of the present invention.

Embodiments of FIGS. 7–8

As seen in FIGS. 7–8, the plate in accordance with the second and third embodiments of the invention does not necessarily need to be ring-shaped, and can be any shape that would correct hyperopia or astigmatism. For example, the plate can be semicircular (FIG. 7), for the correction of astigmatism, or the plate can be a two piece ring-shaped plate (FIG. 8) for the correction of hyperopia and/or astigmatism.

As seen specifically in FIG. 7, the plate 34a can be arcuate, and span less than 360°. For example, the plate can span about 180° or less and can be properly positioned for the correction of astigmatism. However, the plate can span any arc desired, such as 90° or any amount less or more than 180°. Furthermore, if desired, it is possible to activate only a certain number of electrodes or a certain area of electrodes, thus making the coagulation of a specific area of the cornea and the precision in which to correct astigmatism even greater.

As seen specifically, in FIG. 8, the plate 34b can be divided into a first portion 50 and a second portion 52. This configuration enables either or both of the portions to be used to correct astigmatism or hyperopia. Only activating one portion can be accomplished, since each portion 50 and 52 is connected in parallel to an electrical source through its own electrical wires 52a and 54a and 52b and 54b, respectively. However, it is noted that the portions 50 and 52 can be wired in series to an electrical source, or one plate can have a first electrical wire connected thereto (i.e., the hot wiring) and one plate can have a second electrical wire connected thereto (i.e., the neutral wiring), so that electricity would pass from the electrodes of one plate through the corneal stroma into the electrodes of the second plate. Furthermore, as described above, if desired, only certain electrodes need be activated or heated to increase the precision of the correction.

Additionally, both of the ring-shaped plates 36 and 34b can have a non-uniform distribution of the electrodes in a portion of the circular ring on electrodes. This non-uniform distribution will allow simultaneous correction of hyperopia and astigmatism without performing the method multiple times.

Other than the ring-shaped configuration of the first embodiment of FIGS. 1–6, the description of the first embodiment and its method of use are applicable to the plate configurations of the second and third embodiments of FIGS. 7–8.

While various advantageous embodiments have been chosen to illustrate the invention, it will be understood by those skilled in the art that various changes and modifications can be made therein without departing from the scope of the invention as defined in the appended claims.

What is claimed is:

1. A device for reshaping the cornea to correct the refractive error thereof, the device comprising:
   a first electrode adapted to be heated and inserted into the corneal stroma of the eye without passing through the endothelium, thereby reshaping a portion of the cornea;
   a second electrode adapted to be heated and inserted into the corneal stroma of the eye without passing through the endothelium, thereby reshaping a portion of the cornea;
   a plate coupling the first and the second electrodes together, said plate adapted to be curved such that it can substantially conform to the natural curvature of the cornea; and
   a power source for supplying electricity to said first and second electrodes, wherein said electricity is adapted to pass from said first electrode through at least a portion of the corneal stroma and to said second electrode, wherein the power source is programmed to supply electricity to heat at least the portion of the corneal stroma substantially without damaging the Bowman' layer at least partly using the first or the second electrode.

2. A device for reshaping the cornea according to claim 1, wherein
   said plate is a substantially ring-shaped plate.

3. A device for reshaping the cornea according to claim 1, wherein
said plate is a substantially arcuate shaped plate.

4. A device for reshaping the cornea according to claim 1, wherein
said first and second electrodes are substantially the same lengths, so that they are inserted into the cornea of the eye at substantially the same time.

5. A device for reshaping the cornea according to claim 1, further including
third and fourth electrodes coupled to said plate, said third and fourth electrodes adapted to be heated and inserted into the cornea of the eye.

6. A device for reshaping the cornea according to claim 5, wherein
said first, second, third and fourth electrodes form two rows of electrodes.

7. A device for reshaping the cornea according to claim 5, wherein
said plate is a substantially ring-shaped plate; and
said first, second, third and fourth electrodes are equally spaced about the center of said plate.

8. A device for correcting the refractive error in the cornea of an eye, comprising:
a first electrode having a first electrical pole adapted to be inserted into the corneal stroma without passing through the endothelium;
a second electrode having a second electrical pole, opposite said first electrical pole, and adapted to be inserted into the corneal stroma without passing through the endothelium, and coupled to said first electrode, so that when a portion of said first electrode is inserted into the cornea, a portion of said second electrode is inserted into the corneal stroma;
a member coupling said first electrode to said second electrode, said member configured such that it can substantially conform to the natural curvature of the cornea; and
a power source for supplying electricity to said first and second electrodes, wherein said electricity passes from said first electrode through said cornea and to said second electrode, wherein the power source is programmed to supply electricity substantially without killing the cells of the portion of the corneal stroma.

9. A device for correcting the refractive error in the cornea of an eye according to claim 8, and further including at least eight additional electrodes.

10. A device for correcting the refractive error in the cornea of an eye according to claim 9, wherein
said electrodes form a ring.

11. A device for correcting the refractive error in the cornea of an eye according to claim 9, wherein
said electrodes are positioned relative to each other, such that they form an arc.

12. A device for correcting the refractive error in the cornea of an eye according to claim 9, wherein
said electrodes are positioned to form at least two rows.

13. A device for correcting the refractive error in the cornea of an eye according to claim 9, wherein
said at least ten electrodes are positioned to form at least four columns, each column positioned equidistant from each adjacent column.

14. A device for correcting the refractive error in the cornea of an eye according to claim 9, further including
a device to monitor the temperature of the electrodes and control the electricity that passes therethrough.

15. A device for reshaping the cornea to correct the refractive error thereof, the device comprising:
a first electrode adapted to be heated and inserted into the corneal stroma of the eye without passing through the endothelium, thereby reshaping a portion of the cornea;
a second electrode adapted to be heated and inserted into the corneal stroma of the eye without passing through the endothelium, thereby reshaping a portion of the cornea;
a plate coupling the first and the second electrodes together, said plate adapted to be curved such that it can substantially conform to the natural curvature of the cornea; and
a power source for supplying electricity to said first and second electrodes, wherein said electricity is adapted to pass from said first electrode through at least a portion of the corneal stroma and to said second electrode, wherein the power source is programmed to supply electricity to heat said first and second electrodes without killing a substantial number of cells of the corneal epithelium.

* * * * *